United States Patent [19]
Fehr et al.

[11] Patent Number: 5,557,037
[45] Date of Patent: Sep. 17, 1996

[54] SOYBEANS HAVING ELEVATED CONTENTS OF SATURATED FATTY ACIDS

[75] Inventors: Walter R. Fehr; Earl G. Hammond, both of Ames, Iowa

[73] Assignee: Iowa State University Research Foundation, Inc., Ames, Iowa

[21] Appl. No.: 375,340

[22] Filed: Jan. 19, 1995

Related U.S. Application Data

[63] Continuation of Ser. No. 101,407, Aug. 3, 1993, abandoned, which is a continuation of Ser. No. 643,277, Jan. 22, 1991, abandoned, which is a continuation-in-part of Ser. No. 461,341, Jan. 5, 1990, abandoned, which is a continuation-in-part of Ser. No. 445,393, Dec. 5, 1989, abandoned.

[51] Int. Cl.$^6$ .............................. A01H 5/00; A01H 5/10; C12N 15/01
[52] U.S. Cl. .................. 800/200; 800/205; 800/230; 800/255; 800/DIG. 26; 800/DIG. 69
[58] Field of Search ........................... 800/200, 205, 800/230, 255, DIG. 26, DIG. 69

[56] References Cited

U.S. PATENT DOCUMENTS 5,443,974  8/1995  Hitz et al. ........................ 435/172.3

OTHER PUBLICATIONS

Graef et al 1985 J. Amer. Oil Chem. Soc. 62: 773–775.
Erickson et al 1988 J. Heredity 79: 465–468.
Fehr et al 1991 Crop Sci 31: 1522–1524.
Graef et al 1985 Crop Sci 25: 1076–1079.
Hammond et al 1984 J. Amer Oil Chem Soc. 61:1713–1716.
Bubeck et al 1989 Crop Sci 29: 652–656.
Wilcox 1989 In World Soybean Res. Conf. IV Proceedings pp. 28–39.
Iowa Agric & Home Ec. Exper. Station Report 92 (May 1990) pp. 31 and 35.

*Primary Examiner*—Patricia R. Moody
*Attorney, Agent, or Firm*—Burns, Doane, Swecker & Mathis, L.L.P.

[57] ABSTRACT

A method is described for producing soybean varieties and lines exhibiting palmitic acid content of at least about 14.0% and a stearic acid content of at least about 14.0%. Such high saturated fatty acid content soybeans may also, if desired, have a linolenic acid content of less than about 3.0%. The novel soybean lines are obtained by crossing A6 and A17 or by crossing A89-259098 with AX4663-5-4-5.

24 Claims, No Drawings

SOYBEANS HAVING ELEVATED CONTENTS OF SATURATED FATTY ACIDS

This application is a continuation of Ser. No. 08/101,407, filed Aug. 3, 1993 (now abandoned), which is a continuation of Ser. No. 07/643,277, filed Jan. 22, 1991 (now abandoned), which is a continuation-in-part of Ser. No. 07/461,341, filed Jan. 5, 1990 (now abandoned), which is a continuation-in-part of Ser. No. 07/445,393, field Dec. 5, 1989 (now abandoned).

FIELD OF THE INVENTION

This invention relates to novel soybean seeds and products of soybean seeds, such as soybean oil, and, more particularly, to soybean seeds and products characterized by extremely high levels of saturated fatty acids, specifically palmitic acid and stearic acid.

BACKGROUND OF THE INVENTION

Soybean seeds represent perhaps the most significant oil seed in the world. Approximately 28% of the world's supply of fats and oils is derived from soybean oil. More than 90% of this soybean oil is used in food products. In the United States, soybean oil is considered to be the major vegetable oil that is produced and consumed. (World Soybean Research Conference III Proceeding, Shibles, R., Editor. 1985)

Soybeans also provide an excellent source of protein. As such, soybeans represent a potential alternative to meat. Tofu and soymilk are the two principal food products derived from soybean seeds. More than one billion people in China and Southeast Asia, it has been stated, rely on tofu as a major food protein source (Proceedings of the International Soya Protein Food Conference, American Soybean Association, p. 35, 1978). Soymilk is similarly an important source for food protein.

Soybean oil contains five different types of fatty acid. These five types of fatty acids are: palmitic acid (16:0), stearic acid (18:0), oleic acid (18:1), linoleic acid (18:2), and linolenic acid (18:3). Palmitic acid and stearic acid represent the two saturated fatty acids. Palmitic acid averages approximately 11% of the total fatty acids whereas stearic acid averages about 4% of the total fatty acids present in conventional soybean oil.

One application for which soybean oil may be used is the production of plastic fat (e.g., shortening and margarine). Plastic fats are composed of a solid fat matrix, the interstices of which are filled with liquid oil. Solid fats that can crystallize in what is commonly designated as the beta prime (B') form generally have a melting point and other physical properties which are usually desirable for use as a matrix in a plastic fat. In order for a solid fat to stabilize in the B' form for use in a matrix of a plastic fat, it is desirable to have a fatty acid composition of about 15% or more of palmitic acid. The fat may convert from the B' form to the beta (B) form if less than about 15% palmitic acid is present. Although the B form has a higher melting point and greater stability, it has a less desirable physical structure. Accordingly, it would be highly desirable to be able to provide soybean varieties having sufficiently elevated palmitic acid and stearic acid contents so that plastic fat can be produced with the matrix stabilized in the B' form.

Further, the use of soybean oil having a relatively high content of saturated fatty acids should allow production of a more desirable plastic fat. Thus, the higher solid fat content of such soybean oils would be considered more desirable. For example, the use of such a relatively high saturated fatty acid content soybean oil should allow production by interesterification of a plastic fat having substantially higher saturated triglyceride content than can be obtained from soybean oil having the conventional saturated fatty acid content.

It may be desirable for certain applications to utilize soybean oil having relatively high palmitic and stearic acid levels to use, in effect, as a concentrate to be mixed with ordinary soybean oil so as to provide the desired levels of saturated fatty acids. There are potentially other applications for soybean oils having high levels of palmitic acid and stearic acid. For example, such oils might be of interest as a frying oil having increased stability to oxidation compared with ordinary soybean oil. Such oils might also be of interest as raw materials for the production of palmitic and stearic acids and their derivatives.

Palmitic acid levels in soybean seed oil range from 9.3% to 17.4% within the world collection (Erickson et al., Journal of Heredity, Vol. 79, p. 465, 1988). Erickson et al. reports the inheritance of altered palmitic acid percentages in two soybean mutants, C1726 and C1727. The level of palmitic acid in C1727 reportedly averages 17.3% palmitic acid in comparison to 11.5% in the oil of the parent cultivar "Century". Palmitic acid levels reported for soybean seed oil within the world collection are significantly higher than stearic acid levels, which average about 4% of the total fatty acid content.

Applicants' copending application, Ser. No. 445,393, filed Dec. 5, 1989, discloses soybeans exhibiting an endogenous linolenic acid content of less than about 3.0% and a stearic acid content of at least about 20% of the total fatty acid composition. Applicants' copending application, Serial No. 07/461,341, filed Jan. 5, 1990, discloses soybeans exhibiting an endogenous palmitic acid content of at least about 18% of the total fatty acid composition, preferably greater than 20 or even 25%.

Despite the clear need for soybeans having high levels of both palmitic and stearic acids, this objective still remains to be achieved. It would be even further desirable to be able to provide soybeans not only having both high levels of palmitic and stearic acids, but also to have a relatively low linolenic acid content.

SUMMARY OF THE INVENTION

It has been discovered that crossing particular soybean lines provides a population of soybean seeds exhibiting significantly high levels of both palmitic and stearic acid. The palmitic acid concentration obtained is at least about 14% of the total fatty acid composition whereas the stearic acid concentration obtained is at least about 14% of the total fatty acid composition. Preferably, the high palmitic acid content of the soybean lines of the present invention is at least about 15%, and the stearic acid content is at least about 20% or more.

The soybean germplasm so developed thus has the highest content of saturated fatty acids known in soybeans. The combination of elevated palmitic and stearic acids has never been achieved previously in soybeans. Indeed, from applicants' perspective, there was doubt that the biochemical pathways in a soybean plant could be modified to obtain such elevated levels of both saturated fatty acids in the same plant.

In accordance with a more specific aspect of this invention, it has been discovered that soybeans may be provided which are characterized not only by a high saturated fatty acid content, but also by a relatively low linolenic acid content. To this end, high saturated fatty acid content soybean germplasm has been developed that also has a linolenic acid content of less than about 3.0%.

If desired, the soybeans of the present invention can be used in a backcrossing program with any desired commercial cultivar as a recurrent parent to isolate a variety having desirable seed yield and other agronomic characteristics, in addition to the elevated levels of palmitic and stearic acids. Suitable backcrossing techniques are known.

DETAILED DESCRIPTION OF PREFERRED EMBODIMENT

The novel soybean seeds and plants of the present invention, characterized by elevated levels of palmitic acid and stearic acid, were obtained by crossing specifically selected soybean lines. In one embodiment, the soybeans of the present invention were obtained by crossing line A6 with line A17. Line A6 is a mutant line that was identified in a mutation breeding program conducted by the Iowa Agriculture and Home Economics Experiment Station to improve the quality of soybean oil. It has a stearic acid composition that is about 28% of the total fatty acid composition. This is approximately 6–7 fold higher than the percentage of stearic acid found in its parent line FA8077. The A6 line was released for research studies on oil quality and oil biochemistry and for use as a parent stock in soybean breeding and genetics programs. Seed of A6 will be distributed by the Committee for Agricultural Development at Iowa State University, Ames, Iowa. A6 seed will be maintained by the Iowa Agriculture and Home Economics Experiment Station. The soybean variety A6 also has been deposited at the American Type Culture Collection (ATCC) at 12301 Parklawn Drive, Rockville, Md. 20852, U.S.A. More specifically 2,500 seeds of A6 were deposited on Dec. 26, 1995 and have been assigned ATCC Accession No. 97392.

The soybean variety A17 has been deposited under the Budapest Treaty in the American Type Culture Collection (ATCC) at 12301 Park Lawn Drive, Rockville, Md. 20852, U.S.A. A17 has been assigned ATCC Accession No. 40539. More specifically, 625 seeds of A17 were deposited on Jan. 10, 1989. An additional 1,175 seeds of A17 were deposited on Dec. 19, 1995, and an additional 1,325 seeds were deposited on Apr. 22, 1996. The A17 variety has a somewhat elevated palmitic acid content as can be seen from the Examples.

Crossing of the parent lines A6 and A17 to obtain the soybean line of the present invention can be carried out by any desired hybrid formation technique. Standard hybridization techniques are, of course, well known and may be utilized. As an illustrative example, hybridization techniques are disclosed in Fehr, *Principles of Cultivar Development*, Vol. I, Theory and Technique, Chapter 13, pp. 156–164, MacMillan Publishing Company, New York, 1987, which hybridization techniques are herein incorporated by reference.

In accordance with another embodiment, the soybean lines of the present invention were obtained by crossing line AX4663-5-4-5 with line A89-259098. Line AX4663-5-4-5 is derived from ElginEMS-421 and A1937NMU-85, as is described in our copending application, Ser. No. 461,341, the disclosure of which is herein incorporated by reference. 2,500 seeds of AX4663-5-4-5 were deposited on Dec. 26, 1995 at the American Type Culture Collection (ATCC) at 12301 Parklawn Drive, Rockville, Md. 20852, U.S.A. and have been assigned ATCC Accession No. 97393.

A89-259098 is a relatively high stearic acid content soybean line. Its parentage traces to line A6 and a high-yielding experimental line A79-135010 (a line selected from the cross Pride B216 with Cumberland). 1,250 seeds of A89-259098 were deposited on Dec. 26, 1995 at the American Type Culture Collection (ATCC) at 12301 Parklawn Drive, Rockville, Md, 20852, U.S.A. and have been assigned ATCC Accession No. 97391. An additional 1,250 seeds of A89-259098 were deposited on Apr. 22, 1996.

The fatty acid composition was determined by gas-liquid chromatography using the method as generally outlined in Graef et al. (*Crop Science*. 25: 1076–1079, 1985). In general, the method comprises:

(1) crushing the seed sample, (2) putting the crushed sample into a test tube with a hexane solvent and extracting the oil into the hexane, (3) converting the fatty acids in the oil to their methyl esters by using sodium methoxide and methanol, (4) inactivating the sodium methoxide catalyst by adding water, (5) diluting the methyl esters, which float to the top of the water-methanol layer, with hexane for use as sample to be introduced into the column of the gas chromatography apparatus.

As may be appreciated, this general methodology may be employed and specific aspects changed to lessen the time needed as desired. For example, the stationary phase selected for the columns will dictate the temperature at which the sample can be introduced.

None of the specifics utilized, e.g., capillary vs. packed columns, are considered to affect to any appreciable extent the results obtained for an analysis. Rather, such specifics affect the time required for sample preparation and analysis.

The percentages of the fatty acids set forth herein, unless otherwise designated, thus are on a weight basis and refer to the percentage of the methyl ester of palmitic acid or stearic acid compared to the total methyl esters of the fatty acid composition in the sample being analyzed. This can also be taken as the weight percentage of the fatty acid in the total fatty acids present in the sample because the difference between the palmitic or stearic acid percentages in total fatty acids and those of the methyl esters in the total methyl esters is so minimal as may be ignored, as is commonly done in this field.

The gas chromatography techniques described herein are routinely used for analysis of the fatty acid composition of soybeans. The experimental error is considered to be within the range of from about 1 to 5% or so, depending upon the magnitude of the peak. For example, with the relatively large peak indicative of an oleic acid content of 50% or so, the experimental error may be as low as about 1% of the value, viz., 50%±0.5%. At the other extreme, a small peak indicative of a linolenic acid content of 2% may have an experimental error of about 5% of the value, viz., 2%±0.1%. The experimental error associated with the palmitic and stearic acid levels should be intermediate, e.g., about 2 to 3% of the value.

As may be appreciated, the palmitic acid and stearic acid levels of the soybeans of the present invention set forth herein were obtained from soybeans grown in Iowa and Puerto Rico. Growth under climatic conditions cooler or warmer may result in a somewhat altered fatty acid composition. However, while the specific results may vary somewhat, depending upon the specific growing conditions experienced, the progeny of the present invention will be characterized by extremely high palmitic acid content and extremely high stearic acid content relative to other soybean lines grown under similar conditions.

The soybean lines of the present invention are thus characterized by at least about 14% palmitic acid and at least about 14% stearic acid. It is preferred, in the soybeans of this invention, to have a palmitic acid content of at least about 15%, and more preferably, at least about 17%, to insure that, when used to produce a plastic fat, the matrix is stabilized in the B' form. Indeed, for some applications, it is more desirable to have a palmitic acid content of at least about 20%. It is preferred to have a stearic acid content of at least about 20% or, more preferably, at least about 25%. Palmitic acid levels of up to about 30% or more and stearic acid levels of up to about 32% or more should be possible.

The total saturated fatty acid content of the soybean lines is accordingly at least about 28% or so, preferably 35 to 37%, more preferably at least about 45%, and may comprise up to about 60–62% or more of the total fatty acid composition. The particular application will generally dictate the desired total saturated fatty acid content for the soybean germplasm. However, pursuant to the present invention, not only can extremely high saturated fatty acid content soybeans be provided, but the relative levels of the palmitic and stearic acid contents can be varied to tailor the specific acid contents to the particular needs of the application. In similar fashion, soybeans having the desired palmitic and stearic acid contents may be provided with various contents of oleic, linoleic, and linolenic acids as may be considered appropriate for particular applications. Still further, it is within the scope of the present invention to alter the soybeans of this invention by inclusion (by genetic alteration or by other means) of other fatty acids as may be desired. Indeed, as may be appreciated, it is within the scope of the present invention to alter the soybeans of this invention in whatever fashion is considered appropriate for a particular application so long as the high palmitic and stearic acid contents representative of the soybeans of this invention are retained.

Pursuant to a more specific aspect of the present invention, soybeans are provided that not only have high saturated fatty acid contents but also a linolenic acid content of less than about 3.0%. It has thus been discovered that selected progeny from crossing line A6 with line A17 are characterized by the high saturated fatty acid contents previously described and also have a linolenic acid content of less than about 3.0%.

Progeny exhibiting the desired high palmitic acid trait and the desired high stearic acid trait can be crossed with other progeny to provide a population of soybean seeds having extremely high palmitic and stearic acid contents. It can be expected that crosses utilizing the more desirable progeny should be capable of providing lines having palmitic acid contents of up to even about 30% palmitic acid and about 32% stearic acid or more. Where this trait is needed, the more desirable progeny should be capable of providing lines having linolenic acid contents of no more than about 2.5%, perhaps down to 2.0% or so.

Further, progeny can be crossed, if desired, with other progeny, or with any other soybean line or cultivar to yield a soybean cultivar having the desired seed yield or other desired agronomic traits as well as the desired high palmitic acid and high stearic acid traits. Self-pollination of selected progeny may likewise yield lines having characteristics desired for some applications.

Any hybridization technique may be used, and many are known as has been described herein. For example, the selection of progeny having the desired high palmitic acid trait and high stearic acid trait can be obtained by conducting backcrossing with a commercial variety until a desired commercial variety has been isolated. Backcrossing techniques are known, as disclosed in Fehr, *Principles of Cultivar Development,* Volume I, Theory and Technique, Chapter 28, pp. 360–376, the disclosure of which is herein incorporated by reference.

As one example, backcrossing using the desired $F_2$ seeds, obtained by natural self-pollination of the $F_1$ plants, could be carried out as follows:

(1) Plant $F_1$ seeds, obtained by crossing a parent with the desired high palmitic acid and high stearic acid traits to the desired commercial cultivar (recurrent parent). Sample $F_2$ seeds from $F_1$ plants are analyzed for fatty acid concentration, and seeds with the desired high palmitic acid content and high stearic acid content are planted for backcrossing.

(2) Cross-pollinate the desired commercial cultivar (recurrent parent) with an $F_2$ plant having high palmitic acid and high stearic acid content.

(3) Plant the $BC_1F_1$ seeds and obtain $BC_1F_2$ seeds by natural self-pollination. Sample $BC_1F_2$ seeds are analyzed for fatty acid concentration, and those displaying the high palmitic acid and high stearic acid traits are backcrossed to the recurrent parent.

(4) The backcross selection procedure herein describe (step 3) can be repeated until lines with the desired high palmitic acid and high stearic acid composition and agronomic performance are recovered. It is believed that four of these backcross cycles should serve to transfer the high palmitic acid and high stearic acid traits to the desired cultivar (viz., recurrent parent), although the number of such cycles can be fewer, or more, as is desired. The result is the production of a soybean line quite similar to the commercial cultivar, except having the desired high palmitic acid and high stearic acid content.

Any commercial cultivar (recurrent parent) desired may be employed for backcrossing. Factors such as, for example, seed yield, geographical area, and many others, as is known, will generally dictate the cultivar selected from the several hundred commercial cultivars available.

The following Examples are illustrative, but not in limitation, of the present invention. The gas chromatography results obtained from the instrument itself are reported to two decimal points (i.e., . "0.00"). As reported herein, the fatty acid values are set forth to one decimal point. Values of 6 or more in the second decimal point were raised (e.g., 28.29 is reported herein as 28.3), values of 4 or less are ignored (e.g., 28.24 is reported as 28.2), values of 5 are raised if the first decimal is odd (e.g., 28.15 is reported as 28.2) and ignored if even (e.g., 28.25 is reported as 28.2).

EXAMPLE 1

This Example describes the crossing of line A6 with A17 to obtain the soybean lines of the present invention characterized by high palmitic acid and high stearic acid content.

Crosses were made between individual plants of A6 and A17 at the Agricultural Engineering and Agronomy Research Center near Ames, Iowa, during the summer of 1988. The hybrid $F_1$ seeds obtained from the crosses were designated AX5083.

The $F_1$ seed was planted in the Iowa State University-University of Puerto Rico nursery at Isabela, Puerto Rico, in October, 1988. $F_2$ seeds were obtained by natural self-pollination of the $F_1$ plants. Each $F_1$ plant was harvested individually. The $F_2$ seeds of each plant were maintained as a separate subpopulation.

Fourteen $F_2$ seeds from each of the $F_1$ plants and seeds of the parent lines, A6 and A17, were planted in Puerto Rico in February, 1989. $F_3$ seeds were obtained by natural self-pollination of the $F_2$ plants. Seven $F_2$ plants derived from each $F_1$ plant were harvested individually, and a 10-seed sample from each was analyzed for fatty acid composition by gas chromatography. Segregation for palmitic and stearic acid was observed among the $F_2$ progeny from each $F_1$ plant, thereby confirming that each $F_1$ plant was a true hybrid.

A sample of 100 $F_2$ seeds for the population AX5083 and seeds of the parents were planted at Ames, Iowa, in May, 1989. Fifty-eight $F_2$ plants of AX5083 were harvested individually. A 10-seed sample from each $F_2$ plant and from each of the parent lines were analyzed for fatty acid composition by gas chromatography.

Table I summarizes the analysis of the fatty acid composition of the $F_3$ seed from the $F_2$ plant AX5083-3 from Ames, Iowa, having the desired high palmitic acid and high stearic acid content, and that of the parent lines:

TABLE I

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX5083-3 | 17.1 | 28.8 | 16.1 | 32.9 | 5.1 |
| A6 | 8.6 | 29.2 | 17.4 | 38.9 | 5.9 |
| A17 | 15.7 | 5.0 | 26.6 | 50.5 | 2.2 |

Individual $F_3$ seeds from the $F_2$ plant AX5083-3 were cut into two parts with a razor blade. The part containing the embryonic axis (used for planting) was approximately two-thirds of the seed, and the cotyledonary part (used for fatty acid analysis) was approximately one-third of the seed. The identity of all seeds was maintained during analysis, planting, and harvest. Table II summarizes the analysis of the fatty acid composition:

TABLE II

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX5083-3-4 | 15.3 | 24.7 | 14.9 | 39.1 | 6.0 |
| A6 | 8.3 | 29.9 | 21.9 | 34.9 | 5.1 |
| A17 | 17.0 | 4.5 | 27.3 | 49.0 | 2.1 |

The part of the $F_3$ seed AX5083-3-4 containing the embryonic axis was planted in Puerto Rico in February, 1990. The $F_3$ plant AX5083-3-4 was harvested individually.

$F_4$ seed from $F_3$ plant AX5083-3-4 was planted at Ames, Iowa, in June, 1990, and 10 $F_4$ plants were harvested individually. A 10-seed sample from each $F_4$ plant and from each of the parent lines were analyzed for fatty acid composition by gas chromatography.

Table III summarizes the average analysis of the fatty acid composition of ten $F_4$ plants from the $F_3$ plant AX5083-3-4 as well as that of the parents:

TABLE III

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX5083-3-4 | 16.2 | 26.4 | 17.4 | 34.3 | 5.7 |
| A6 | 8.5 | 27.2 | 18.5 | 39.6 | 6.2 |
| A17 | 14.2 | 4.4 | 42.7 | 36.8 | 1.8 |

EXAMPLE 2

This Example describes the crossing of AX4663-5-4-5 with line A89-259098 to obtain the soybean lines of the present invention characterized by high palmitic and high stearic acid content.

Parent line AX4663-5-4-5 was obtained as set forth in our co-pending application, Ser. No. 461,341, the disclosure of which is incorporated herein by reference, as previously discussed.

Parent line A89-259098 was obtained by backcrossing A6 (donor parent) to a high yielding experimental line A79-135010 (recurrent parent).

Crosses were made between individual plants of line AX4663-5-4-5 and A89-259098 at the Iowa State University-University of Puerto Rico nursery at Isabela, Puerto Rico, in December, 1989. The hybrid $F_1$ seeds obtained from the cross were designated AX7016-AX7019.

The $F_1$ seed was planted in Puerto Rico in February, 1990. $F_2$ seeds were obtained by natural self-pollination of the $F_1$ plants. Each $F_1$ plant was harvested individually. The $F_2$ seeds of each plant were maintained as a separate subpopulation.

Four $F_2$ seeds from each $F_1$ plant were split, and the non-embryo portion of the $F_2$ seeds was analyzed for fatty acid composition by gas chromatography. The embryo portion of selected $F_2$ seeds was planted at the Agricultural Engineering and Agronomy Research Center near Ames, Iowa, in May, 1990. $F_3$ seeds were obtained by natural self-pollination of the $F_2$ plants. Each $F_2$ plant was harvested individually. Thirteen $F_3$ seeds from each $F_2$ plant were split, and the non-embryo portion of the seeds was analyzed for fatty acid composition by gas chromatography.

Table IV summarizes the mean fatty acid composition of $F_3$ seeds from $F_2$ plant AX7019-1-2 and, as controls, seeds of lines having traits considered to be similar to those of the parents:

TABLE IV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX7019-1-2 | 23.6 | 24.1 | 8.0 | 37.4 | 6.9 |
| A19 | 29.6 | 4.2 | 15.2 | 44.4 | 6.6 |
| A89-261056 | 8.9 | 26.1 | 16.6 | 43.1 | 5.2 |

EXAMPLE 3

This Example describes the crossing of line A6 with line A17 to obtain the soybean lines of the present invention characterized not only by high palmitic acid and high stearic acid content, but also by a relatively low linolenic acid content.

The crosses designated AX5083 were made as previously described in Example 1, as are the respective plantings. Likewise, individual $F_3$ seeds from the $F_2$ plant AX5083-2 were analyzed as described in Example 1 for the $F_3$ seeds from the $F_2$ plant AX5083-3. Table V summarizes the analysis of the fatty acid composition of the $F_3$ seed AX5083-2-8:

TABLE V

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX5083-2-8 | 14.2 | 25.6 | 19.5 | 38.2 | 2.6 |
| A6 | 8.3 | 29.9 | 21.9 | 34.9 | 5.1 |
| A17 | 17.0 | 4.5 | 27.3 | 49.1 | 2.1 |

The part of the $F_3$ seed AX5083-2-8 containing the embryonic axis was treated as described in Example 1 for AX5083-3-4, and $F_4$ seed from $F_3$ plant AX5083-2-8 was planted in Ames as described in Example 1.

Table VI summarizes the average analysis of the fatty acid composition of the ten $F_4$ plants from the $F_3$ plant AX5083-2-8 as well as that of the parents:

TABLE VI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX5083-2-8 | 16.0 | 21.1 | 18.5 | 42.0 | 2.3 |
| A6 | 8.5 | 27.2 | 18.5 | 39.6 | 6.2 |
| A17 | 14.2 | 4.4 | 42.7 | 36.8 | 1.8 |

Although the foregoing invention has been described in detail with examples for the purpose of understanding the invention, it will be understood by those skilled in the art that various modifications of the invention may be practiced, while remaining within the spirit and the scope of the appended claims.

We claim:

1. A soybean plant which produces upon self pollination mature seed containing an endogenous palmitic acid content of from about 14% to about 24% of the total fatty acid composition and an endogenous stearic acid content of from about 20% to about 30% of the total fatty acid composition.

2. A soybean plant according to claim 1 which yields upon self pollination a mature seed that contains an endogenous palmitic acid content of about 15%.

3. A soybean plant according to claim 1 which yields upon self pollination a mature seed that contains an endogenous pahnitic acid content of about 17%.

4. A soybean plant according to claim 1 which yields upon self pollination a mature seed that contains an endogenous stearic acid content of about 20%.

5. A mature seed formed upon the self pollination of the soybean plant according to claim 1.

6. A mature seed according to claim 5 that contains an endogenous palmitic acid content of about 15%.

7. A mature seed according to claim 5 that contains an endogenous palmitic acid content of about 17%.

8. A mature seed according to claim 5 that contains an endogenous stearic acid content of about 20%.

9. A soybean plant which includes in its ancestry the product of crossing a first parent designated soybean A6 having ATCC Accession No. 97392 with a second parent designated soybean A17 having ATCC Accession No. 40539, wherein the soybean plant resulting from said cross yields mature seed that contains an endogenous palmitic acid content of from about 14% to about 24% of the total fatty acid composition and an endogenous stearic acid content of from about 20% to about 30% of the total fatty acid composition, and wherein the descendants of said cross retain endogenous palmitic acid and stearic acid contents within said ranges.

10. A soybean plant according to claim 9 which yields upon self pollination a mature seed that contains an endogenous palmitic acid content of about 15%.

11. A soybean plant according to claim 9 which yields upon self pollination a mature seed that contains an endogenous palmitic acid content of about 17%.

12. A soybean plant according to claim 9 which yields upon self pollination a mature seed that contains an endogenous stearic acid content of about 20%.

13. A mature seed formed upon the self pollination of the soybean plant according to claim 9.

14. A mature seed according to claim 13 that contains an endogenous palmitic acid content of about 15%.

15. A mature seed according to claim 13 that contains an endogenous palmitic acid content of about 17%.

16. A mature seed according to claim 13 that contains an endogenous stearic acid content of about 20%.

17. A soybean plant which includes in its ancestry the product of crossing a first parent designated soybean A89-259098 having ATCC Accession No. 97391 with a second parent designated soybean AX4663-5-4-5 having ATCC Accession No. 97393, wherein the soybean plant resulting from said cross yields mature seed that contains an endogenous palmitic acid content of from about 14% to about 24% of the total fatty acid composition and an endogenous stearic acid content of from about 20% to about 30% of the total fatty acid composition, and wherein the descendants of said cross retain endogenous palmitic acid and stearic acid contents within said ranges.

18. A soybean plant according to claim 17 which yields upon self pollination a mature seed that contains an endogenous palmitic acid content of about 15%.

19. A soybean plant according to claim 17 which yields upon self pollination a mature seed that contains an endogenous palmitic acid content of about 17%.

20. A soybean plant according to claim 17 which yields upon self pollination a mature seed that contains an endogenous stearic acid content of about 20%.

21. A mature seed formed upon the self pollination of the soybean plant according to claim 17.

22. A mature seed according to claim 21 that contains an endogenous palmitic acid content of about 15%.

23. A mature seed according to claim 21 that contains an endogenous palmitic acid content of about 17%.

24. A mature seed according to claim 21 that contains an endogenous stearic acid content of about 20%.

* * * * *